United States Patent [19]
Kusch

[11] Patent Number: 5,980,107
[45] Date of Patent: Nov. 9, 1999

[54] APPARATUS HAVING MEANS FOR THE TRANSMISSION OF ELECTRICAL ENERGY AND/OR OF SIGNALS

[75] Inventor: Jochen Kusch, Effeltrich, Germany

[73] Assignee: Siemens Aktiengesellschaft, Munich, Germany

[21] Appl. No.: 08/986,152

[22] Filed: Dec. 5, 1997

[30] Foreign Application Priority Data

Dec. 13, 1996 [DE] Germany .......................... 196 51 960

[51] Int. Cl.$^6$ .................................................. H05G 1/02
[52] U.S. Cl. .............................. 378/194; 439/4; 439/501
[58] Field of Search ..................... 378/193, 194, 378/197, 198; 439/501, 4

[56] References Cited

U.S. PATENT DOCUMENTS 4,802,197  1/1989  Juergens .................................. 378/197
5,145,390  9/1992  Kaul .
5,450,466  9/1995  Kadowaki et al. ..................... 378/194

FOREIGN PATENT DOCUMENTS 89 09 486  of 0000  Germany .

Primary Examiner—David P. Porta
Attorney, Agent, or Firm—Hill & Simpson

[57] ABSTRACT

An apparatus has an arrangement for the transmission, via conductors, of electrical energy and/or signals from an apparatus part to electrical devices which are displaceable relative to the apparatus part. The arrangement has a rotatable reel onto which another conductor is wound when one conductor is unwound.

8 Claims, 2 Drawing Sheets

APPARATUS HAVING MEANS FOR THE TRANSMISSION OF ELECTRICAL ENERGY AND/OR OF SIGNALS

BACKGROUND OF THE INVENTION

1. Field of the Invention

The present invention is directed to an apparatus having a transmission arrangement for the transmission of electrical energy and/or signals from an apparatus part to electrical devices which are displaceable relative to the apparatus part, the transmission arrangement including a reel onto which and from which a conductor can be wound.

2. Description of the Prior Art

For example, German Utility Model 89 09 486 discloses an apparatus of this general type. This known apparatus has two apparatus parts which are adjustable relative to one another and which are connected to one another by the conductor. The transmission arrangement, which is held in one of the two apparatus parts, includes an outer, hollow cylinder-like drum forming a reel that is seated so as to be rotatable around an inner hollow cylinder-like drum that is stationary relative to the outer drum. The respective outer surfaces of these drums have an opening through which the conductor, namely a ribbon conductor, is conducted.

The ribbon conductor is first conducted through a lateral opening of the inner drum, then through the opening in the surface of the inner drum into the region between the drums, and is wound around the inner drum as a helix, and is conducted toward the outside through the opening in the surface of the outer drum. The section of the ribbon conductor that is located between the drums thus has its section ends respectively secured to the inner and outer drums such that the ribbon conductor is wound onto the surface of the outer drum, or is unwound therefrom with the assistance of a guide given rotation of the outer drum around the inner drum. When the ribbon conductor is wound onto or unwound from the outer drum, the helix formed by the region of the ribbon conductor lying between the drums narrows or widens in the direction toward the surface of the inner drum.

Given an adjustment of the two apparatus parts of the apparatus relative to one another, a tensile force or thrust is thus exerted on the ribbon conductor secured to the other apparatus part, causing the outer drum to rotate and thereby effecting the winding or unwinding of the ribbon conductor.

German OS 40 19 513, corresponding to U.S. Pat. No. 5,145,390, discloses an apparatus having two apparatus parts which are adjustable relative to one another and which are connected together by an electrical conductor, which is again a ribbon conductor, and having an arrangement for the acceptance of the ribbon conductor and a cable, the arrangement being held in one of the two apparatus parts. The arrangement includes a rotatable drum onto which or from which the ribbon conductor and the cable, which are secured to the other apparatus part, namely at a one end of the other apparatus part, are wound or unwound in opposite directions on different regions of the drum. Upon exertion of a tensile force onto the ribbon conductor by adjusting the two apparatus parts relative to one another, the ribbon conductor is unwound from and the cable is wound onto the rotatable drum and, given exertion of a tensile force on the cable due to oppositely directed adjustment of the two apparatus parts relative to one another, the cable is unwound from and the ribbon conductor is wound onto the rotatable drum. A spring, by means of which the cable end is secured to the other apparatus part, thereby serves the purpose of exerting a constant tensile force on the cable, and thus on the ribbon cable as well, so that this is wound onto the drum with a slight pre-stress.

Because they operate by rolling up the cable, these known arrangements are structurally complicated devices that are only suitable for winding or unwinding a single cable reliably, i.e. without the formation of loops. Ultimately, they function reliably only with ribbon conductors. Ribbon conductors, however, are expensive and occupy a large space when wound onto a drum.

SUMMARY OF THE INVENTION

An object of the present invention is to provide an apparatus of the type initially described having a simple and economical structure and which allows a reliable winding and unwinding of a number of conductors.

This object is achieved in accordance with the invention in an apparatus having transmission means for the transmission, via electrical conductors, of electrical energy and/or signals from one apparatus part to electrical devices which are displaceable relative to the apparatus part, the transmission means including a rotatable reel onto which a different conductor is wound when another conductor is unwound. In the invention, thus, a number of conductors can be simultaneously reliably wound onto or unwound from the reel. The conductors are either wound onto and unwound from different regions of the reel or, when one conductor is unwound, another conductor is wound onto the space of the reel made available by the unwinding conductor. Since no guides, other types of devices or structural details for assuring a reliable winding and unwinding of the conductors are needed for the winding and unwinding of the conductors onto or of the inventive apparatus from the reel, the structure of the apparatus, particularly of the transmission means, becomes correspondingly simple and economical.

Preferably, an even-number of conductors are provided, these being simultaneously unwound from or wound onto the reel, with a different conductor, or the same number of conductors, are wound onto the reel by the same distance that a conductor or a specific number of conductors are unwound from the reel by a specific distance. As a result, the space requirement of identical conductors wound onto the reel is substantially constant since just as many conductors are always wound onto the reel as are unwound from the reel, and by the same distance.

In a preferred embodiment of the invention, two side-by-side conductors can be wound onto or unwound from the reel such that, when unwinding a conductor by the exertion of a tensile force on this conductor, the other conductor is wound onto the space of the reel formerly occupied by the unwinding conductor. Conductors to be wound up can thus be wound only where space becomes free on the reel due to the unwinding conductors and the tensile forces exerted on the unwinding conductors place the reel into rotation controlled by the opposing forces of the conductors to be wound up. Therefore the turns of the conductors wound onto the reel lie tightly and regularly side-by-side, so that—given identical conductors—substantially no interspaces between the turns of individual conductors occur and the space available on the reel for the conductors is optimally exploited.

According to another preferred embodiment of the invention, the conductors are of round cables with, preferably, substantially the same diameters. In this way, the use of expensive ribbon conductors for the energy and/or signal transmission is replaced by comparatively economical round cables, so that the cost outlay for building the apparatus is reduced overall. Moreover, round cables have a significantly lower space requirement on the reel compared to ribbon conductors.

In another version of the invention the reel has a width so that all turns of individual conductors wound onto the reel lie next to one another. The precondition for a clean winding of the conductors onto and unwinding of the conductors from the reel is established because the turns do not come to lie above one another.

In a further version of the invention, the second apparatus part is fashioned as an arc and engages the first apparatus part, which functions as an arc holder and the second part is seated adjustably at the holder along its circumference. The conductors connect the apparatus parts to one another and one or more conductors are secured to an end of the arc and the other conductor or conductors are secured to the other end of the arc. The winding and unwinding of the conductors can be effected with the same but oppositely directed forces given adjustment of the arc in a first direction and upon exertion of a tensile force on the one conductor or conductors and given adjustment of the arc in a second direction upon exertion of a tensile force on the other conductor or conductors. Thus, the expenditure of force for the adjustment of the arc in the one direction corresponds to the expenditure of force for the adjustment of the arc in the other direction.

According to another embodiment of the invention, at least one conductor is provided for the transmission of energy and at least one conductor is provided for the transmission of signals, and the arc has lines running from one end to the other end that transmit the energy and/or the signals from one end of the arc to the other. By separating energy line and signal line, fewer disturbances due to crosstalk from energy lines onto signal lines and thus fewer disturbances in the operation of the apparatus, occur. Moreover, the use of round conductors for the signal and/or energy transmission also achieves a saving of space on the reel of the apparatus, as already mentioned. Compared to known apparatuses that, for example, employ only one round conductor for energy and/or signal transmission that is wound onto and unwound from a reel, the conductors to be wound onto and unwound from the reel of the inventive apparatus can have a smaller diameter due to the use of a number of conductors for energy and/or signal transmission. This means that the winding volume (conductor length*cross-sectional conductor area) required on the reel is reduced, since only a constant part of the total length of the conductors is always wound on the reel. Moreover, the conductors having a smaller diameter can accommodate a more severe curvature than a conductor having a larger diameter, so that the complete structure for the acceptance of the conductors can be smaller, the space requirement of the overall arrangement being reduced as a result.

DESCRIPTION OF THE PREFERRED EMBODIMENTS

Figure 1:
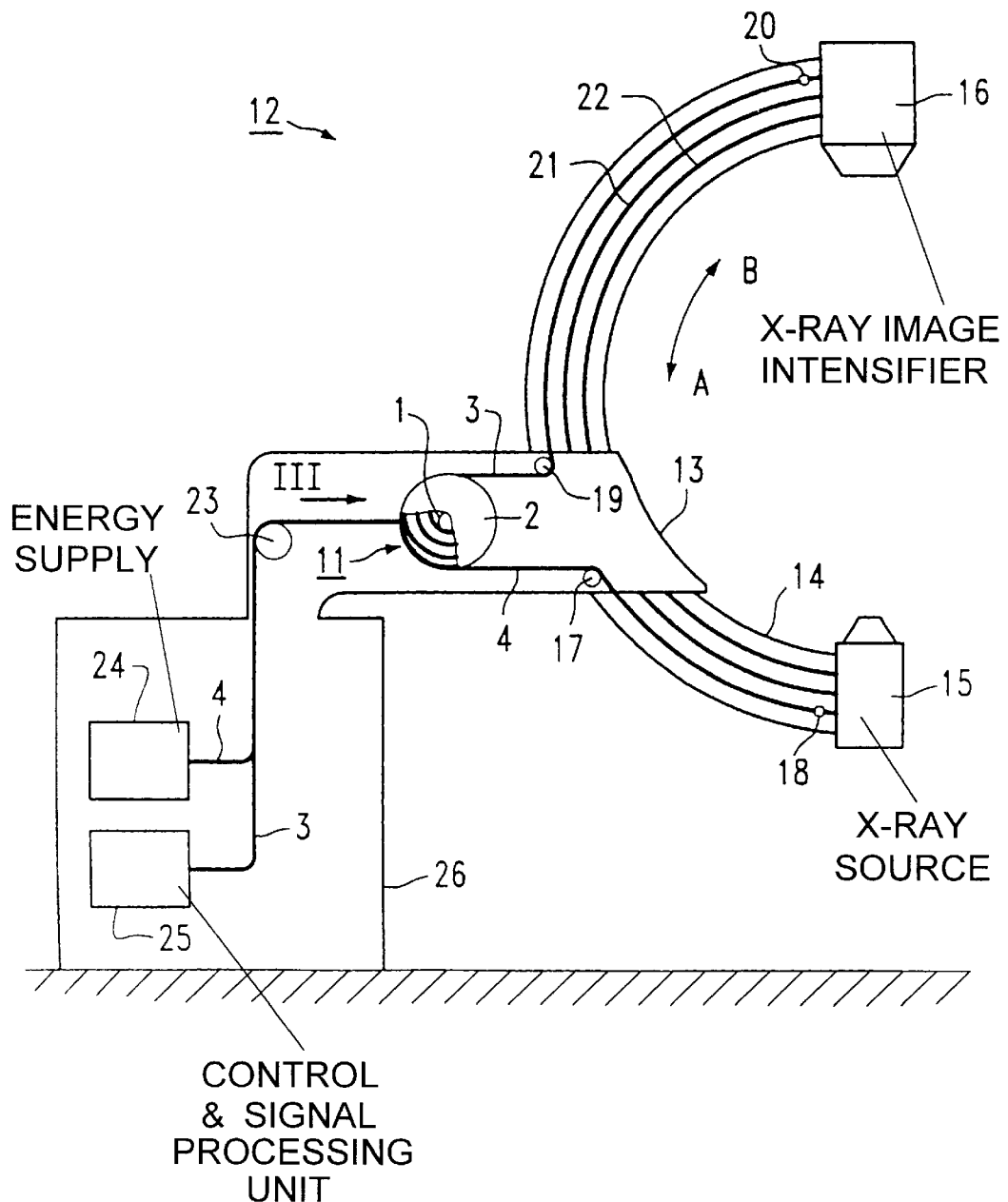
FIG. 1 is a schematic illustration of an inventive apparatus.

FIG. 1 shows an example of an inventive apparatus having an arrangement 11 for the transmission of electrical energy and signals. In the exemplary embodiment, the apparatus is a C-arm X-ray apparatus 12 having a first apparatus part fashioned as holder 13 and having a second apparatus part fashioned as C-arm 14. The C-arm 14 is held adjustably along its circumference by the holder 13. At its ends, the C-arm 14 carries an X-ray source 15 and an X-ray image intensifier 16 opposite one another. The holder 13 is secured to a further apparatus part 26 of the C-arm X-ray apparatus 12, the further apparatus part 26 being an energy supply 24 and a control and signal processing unit 25 for the operation of the X-ray source 15 and the X-ray image a intensifier 16. The control and signal processing unit 25 provides control signals for the drive of the X-ray source 15 and the X-ray image intensifier 16 and also processes image signals acquired by the X-ray image intensifier 16.

Figure 2:
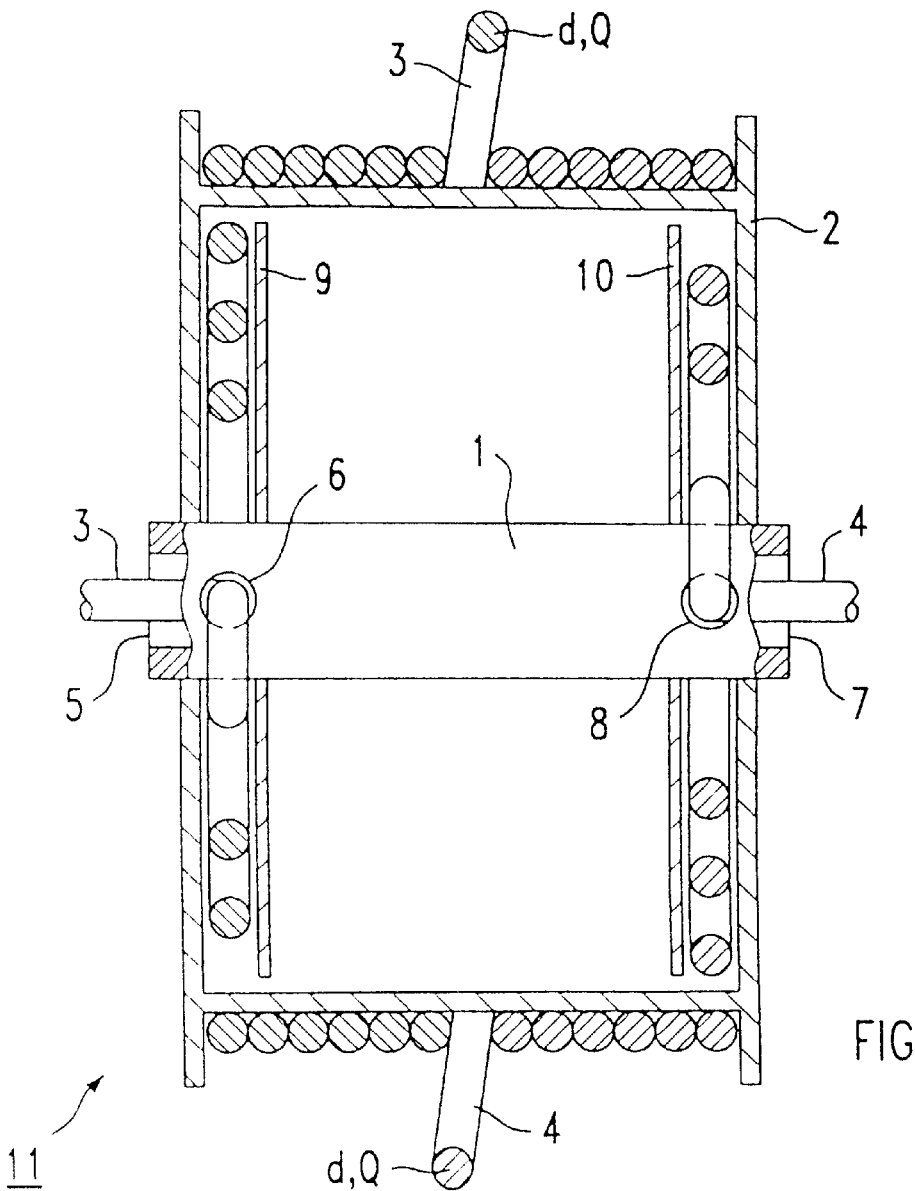
FIG. 2 is a schematic, partially broken away, view of an arrangement for the acceptance of electrical conductors of the inventive apparatus of FIG. 1.

The arrangement 11, described in greater detail below with reference to FIG. 2, is accepted in the holder 13, and has electrical conductors in the form of round cables 3 and 4 having substantially the same diameter d. The cables 3 and 4 connect the C-arm 14, the holder 13 and the apparatus part 26 (that contains the energy supply 24 and the control and signal processing unit 250 to one another.

The arrangement 11 has an inner, hollow cylinder-like reel 1 around which an outer, hollow cylinder-like reel 2 is rotatably seated. The inner reel 1 is stationary with respect to the outer reel 2. The cable 3 is conducted over a deflection roller 23 to the arrangement 11 proceeding from the control and signal processing unit 25 and is conducted into a lateral opening 5 of the inner reel 1 at the arrangement 11 and through an opening 6 in the surface of the inner roller 1 into the region between the reels 1 and 2. In this region, the cable 3 is wound around the inner reel 1 in a helix and is conducted out through an opening (not shown in FIG. 2) in the surface of the outer reel 2. In the regions of the respective openings in the surfaces of the reels 1 and 2, the cable 3 is fixed both to the surface of the inner reel 1 and as to the surface of the outer reel 2. The region of the cable 3 that is conducted out through the surface of the outer reel 2 is accepted by the outer reel 2, onto which the cable 3 can be wound such that the turns of the wound-up cable lie next to one another with substantially no interspaces between individual turns of the cable 3. The cable 3 is conducted from the outer reel 2 of the arrangement 11 over a further deflection roller 19 to one end of the C-arm 14, at which it is secured to a holder 20 of the C-arm 14. In the exemplary embodiment, the X-ray image intensifier 16 to which the cable 3 is conducted is held at that end.

In a way analogous to the cable 3, the cable 4 conducted over the deflection roller 23 to the arrangement 11 proceeding from the energy supply 24 of the apparatus part 26 and is conducted into a second opening 8 in the surface of the inner reel 1, likewise into the region between the reels 1 and 2. In this region, the cable 4 is helically wound around the inner reel 1, but in a winding sense (direction) opposite the cable 3, and is conducted out through a second opening (not shown in FIG. 2) in the surface of the outer reel 2. In the region of the openings in the generated surfaces of the reels 1 and 2, the cable 4 is likewise fixed both to the surface of the inner reel 1 and to the surface of the outer reel 2. The region of the cable 4 that is conducted out through the surface of the outer reel 2 is likewise accepted by the outer reel 2, onto which the cable 3 can be wound in a sense opposite the cable 3 such that the turns of the wound-up cable 4 lie next to one another, with substantially no interspaces between individual turns of the cable 4. From the outer reel 2 of the arrangement 11, the cable 4 is conducted over a deflection roller 17 to the other end of the C-arm 14, at which the X-ray source 15 is attached in the case of the exemplary embodiment. At this end of the C-arm 14, the cable 4 is secured to a holder 18 of the C-arm 14 and conducted to the X-ray source 15.

In the exemplary embodiment, thus, the cable 3 serves for the transmission of control signals from the control and signal processing unit 25 that, as already mentioned, are provided for the X-ray source 15 and the X-ray image intensifier 16. The cable 3 also serves for the transmission of images signals acquired by the X-ray image intensifier 16 from the X-ray image intensifier 16 to the control and signal processing unit 25. The cable 4 serves for the transmission of energy from the energy supply 24 that is provided for the X-ray source 15 and for the X-ray image intensifier 16. Cables 21 and 22 that are provided at the C-arm 14 and transmit the control signals to the X-ray source 15 from the cable 3 together with the control signals for the X-ray image intensifier 16 to the X-ray source 15, and transmit the energy provided for the X-ray image intensifier 16 from the cable 4 together with the energy for the X-ray source 15 to the X-ray image intensifier 16. Inventively, thus, a separation of energy and signal lines ensues in order to avoid disturbing influences due to crosstalk between the energy line and the signal line during operation of the C-arm X-ray apparatus 12.

The cables 3 and 4 are wound onto the outer reel 2 of the arrangement 11 side-by-side, or are unwound from the outer reel 2, such that, when unwinding, the cable 3, for example, by a certain distance from the outer reel 2 upon exertion of a tensile force on the cable 3, the cable 4 is tightly wound by the same distance onto the space of the outer reel 2 freed by the unwound cable 3. The space on the outer reel 2 is thereby always optimally exploited and winding up is reliably assured since the turns when winding up the cable 4 lie cleanly next to one another, practically guided by the turns of the cables 3 and 4 already present on the outer reel 2 in the current winding or unwinding region. In the described winding operation, the outer reel 2 rotates around the inner reel 1 that is stationary with respect to the outer reel 2. The helix formed by the cable 3 between the reels 1 and 2 narrows in the direction toward the surface of the inner reel 1, whereas the helix formed by the cable 4 between the reels 1 and 2 widens in the direction toward the surface of the outer reel 2.

When the cable 4, upon exertion of a tensile force on the cable 4, is unwound from the outer reel 2 by a certain distance, then the rotational sense of the outer reel 2 changes. Simultaneously with the unwinding of the cable 4, the cable 3 is wound by the same distance onto space of the outer reel 2 freed by the unwound cable 4. The relationships in the region between the outer reel 2 and the inner reel 1 are also reversed. In this case, the helix formed by the cable 3 thus widens in the direction toward the generated surface of the outer reel 2, whereas the helix formed by the cable 4 narrows in the direction toward the generated surface of the inner reel 1.

Taking the length L of the regions of the cables 3 and 4 that can be wound onto and unwound from the outer reel 2 and the diameter d of the cables 3 and 4 into consideration, the width of the outer reel 2 is selected such that no turns of the regions of the cables 3 and 4 wound onto the outer reel 2 lie on top of one another but all turns lie next to one another. When the region of the cable 4 that can be wound onto the outer reel 2 is entirely unwound from the outer reel 2, then the region of the cable 3 that can be wound onto the outer reel 2 is entirely wound onto the outer reel 2 and vice versa. Further, the lengths of the regions of the cables 3 and 4 situated between the reels 1 and 2 are selected such that a complete unwinding of the cable 3 or 4 from the outer reel 2 is possible.

In order to prevent twisting and the formation of loops and in order to assure a clean narrowing and widening of the helical regions of the cables 3 and 4, separating disks 9 and 10 that prevent a lateral swerve of the helical regions of the cables 3 and 4 are firmly attached to the inner reel 1.

When, thus, the C-arm 14 in the holder 13 is adjusted in a direction A, then a tensile force is exerted on the cable 4, so that the cable 4 is unwound from the outer reel 2 of the arrangement 11. Simultaneously, the rotation of the outer reel 2 around the inner reel 1—as already mentioned—effects the wind-up of the cable 3 onto the outer reel 2 such that the cable 3 is wound up on the space of the outer reel 2 freed by the unwound cable 4. When, by contrast, the C-arm 14 is adjusted in a direction B, then a tensile force is exerted on the cable 3, the outer reel 2 being placed in rotation in the opposite direction as a result. The cable 3 is thus unwound from the outer reel 2 and the cable 4 is simultaneously wound onto the outer reel 2 in the manner set forth above. A force-neutral adjustment of the C-arm 14 is thus assured, i.e. the force expended for the adjustment of the C-arm 14 in the one direction A corresponds to the force expended for the adjustment of the C-arm 14 in the other direction B.

Figure 3:
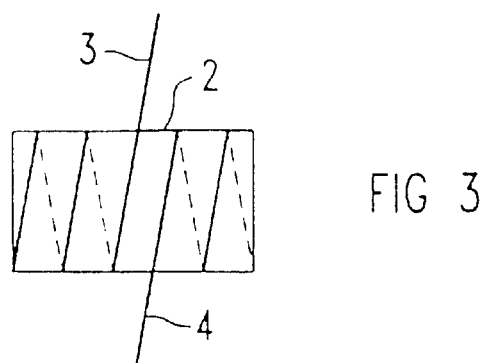
FIG. 3 is a schematic illustration of the view as seen in the direction of the arrow III in FIG. 1.

As seen in the direction of the arrow III from FIG. 1, FIG. 3 schematically shows the lay of the turns of the cables 3 and 4 on the outer roller 2 of the arrangement 11, it being clear that the cable 4 is wound onto the outer reel 2 exactly where the cable 3 was previously unwound, and vice versa.

During the winding and unwinding operations, moreover, essentially no twisting and tensile forces act on the regions of the cables 3 and 4 emerging from the lateral openings 5 and 7 of the inner reel 1, these regions of the cables 3 and 4 being stationary in position during winding an unwinding operations of the cables 3 and 4 onto or from the outer reel 2. The deflection roller 23 via which the cables 3 and 4 are conducted to the energy supply 24 and to the control and signal processing unit 25 thereby accepts the cable 3 as well as the cable 4.

The holder 13, moreover, need not necessarily be rigidly connected to the apparatus part 26. The holder 13 alternatively can be seated adjustably in height and pivotable relative to the apparatus part 26. In this case, however, at least one mechanism that correspondingly readjusts the cables 3 and 4 for the purpose of the height adjustment and pivoting of the holder 13 must also be provided in the holder 13 or in the apparatus part 26.

In the exemplary embodiment of the invention, the energy line and the signal line are implemented separately in the form of the two cables 3 and 4. By contrast, only one cable is employed for the energy and signal transmission in known apparatus. The length of the region of the cable 3 or 4, or of the single cable in the case of the conventional apparatus, must be equal; let this be L. Further, let the cable have a cross-sectional area F and a diameter D. When it is assumed that, due to the use of two cables 3 and 4 whose cross-sectional area Q is substantially equal and can be halved compared to the cross-sectional area F of the one cable ($Q=F/2$, length L, diameter $d=D/\sqrt{2}$), then a halving of the winding volume (length of the region of the cable that can be wound onto the outer roller 2*cross-sectional area) from $L \cdot F$ to $L \cdot F/2$ approximately derives for the arrangement 11 compared to the known apparatus. The outer reel 2 always accepts only half the total length $((2 \cdot l)/2)$ of the regions of the cables 3 and 4 that can be wound onto the outer reel 2. The other half of the total length of the regions of the cables 3 and 4 that can be wound onto the outer reel 2 is always unwound from the outer reel 2.

When it is further assumed that the smallest allowable curvature of the cables 3 and 4 compared to the smallest allowable curvature of the one cable of the example diminishes by the same factor $1/\sqrt{2}$ as the diameter thereof, the outer reel 2 can be implemented correspondingly smaller in diameter, a space saving of approximately 30% deriving overall as a result thereof in the present example.

Further, more than two cables can be wound onto or unwound from a reel with the inventive apparatus, with an even-number of conductors preferably provided. When unwinding the one conductor from the outer reel 2, the other conductors are then wound onto the outer reel 2 of the arrangement. Two conductors thus collaborate, i.e. one conductor being wound onto the space on the outer reel freed by the unwinding conductor. The width of the outer reel is always selected so that no turns lie on top of one another but all turns lie next to one another. This means the outer reel 2 of an arrangement for, for example, six cables of equal diameters has three times the width of a comparable arrangement for two cables, with all cables having the same length L that can be wound onto the outer reel 2.

In the case of a C-arm X-ray apparatus, the arrangement 11 need not necessarily be provided at the holder 13, but can be allocated to the C-arm 14 given an appropriately modified embodiment of the inventive apparatus.

The apparatus that contains the arrangement need not necessarily be a C-arm X-ray apparatus, but be some other apparatus.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus comprising:

an apparatus part and a plurality of electrical devices which are displaceable relative to said apparatus part;

means for transmitting at least one of electrical energy and signals, via at least two conductors, from said apparatus part to said electrical devices, including a rotatable reel onto which one of said conductors is wound while another of said conductors is unwound from said reel; and said two conductors being disposed next to each other on said reel with a first of said two conductors being unwound from said reel upon an application of tensile force to said first of said conductors, thereby leaving an increasing space on said reel, and a second of said conductors being wound onto said space.

2. An apparatus as claimed in claim 1 comprising an even number of said conductors.

3. An apparatus as claimed in claim 1 wherein said conductors comprise substantially round cables.

4. An apparatus as claimed in claim 3 wherein said conductors respectively have substantially equal diameters.

5. An apparatus as claimed in claim 1 wherein said reel has a width allowing all turns of said conductors to be wound onto said reel next to each other.

6. An apparatus as claimed in claim 1 wherein said apparatus part comprises a first apparatus part, and said apparatus further comprising a second apparatus part and means for moving said second apparatus part relative to said first apparatus part, said second apparatus part carrying at least some of said electrical devices and thus being connected to said first apparatus part by said at least two conductors, with movement of said second apparatus part in a first direction exerting a tensile force on a first of said conductors to cause said first of said conductors to be unwound from said reel and a second of said conductors to be wound onto said reel, and movement of said second apparatus part in a second direction causing a tensile force to be exerted on said second of said conductors and causing said second of said conductors to be unwound from said reel while said first of said conductors is wound onto said reel.

7. An apparatus as claimed in claim 6 wherein said second apparatus comprises and arc and wherein said first apparatus part comprises an arc holder in which said arc is movable, and wherein said electrical devices include an X-ray source and an X-ray receiver disposed at opposite ends of said arc, with said first of said conductors being attached at a first end of said arc and a second of said conductors being attached at a second end of said arc.

8. An apparatus as claimed in claim 7 wherein at least one of said conductors exclusively transmits energy and at least another of said conductors exclusively transmits signals, and wherein said arc carries a plurality of electrical winds extending from said first end to said second end, and connected to said at least one conductor and said at least another conductor, for transmitting said energy and said signals between said first and second ends of said arc.

* * * * *